Figure 1:
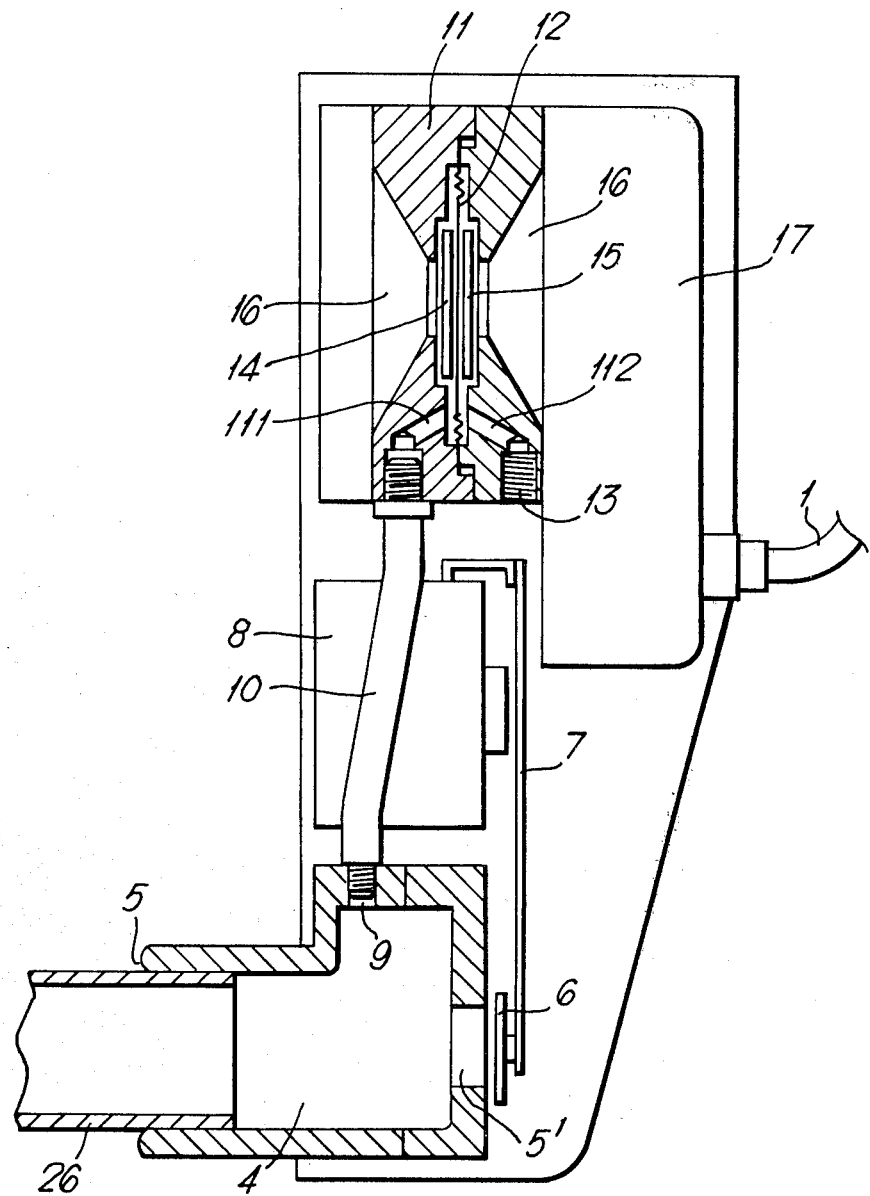

United States Patent [19]

Vooren et al.

[11] 4,259,967

[45] Apr. 7, 1981

[54] APPARATUS FOR THE DETERMINATION OF RESPIRATORY PARAMETERS

[75] Inventors: Pieter H. Vooren, Noordwijkerhout; Klaas H. van der Plas, Katwijk aan Zee, both of Netherlands

[73] Assignee: Vitalograph (Ireland) Limited, Lifford Ennis, Northern Ireland

[21] Appl. No.: 967,885

[22] Filed: Dec. 8, 1978

[30] Foreign Application Priority Data

Dec. 9, 1977 [GB] United Kingdom ............... 51260/77

[51] Int. Cl.³ ................................................. A61B 5/08
[52] U.S. Cl. ................................................... 128/720
[58] Field of Search ........................ 128/720, 724, 725

[56] References Cited

U.S. PATENT DOCUMENTS

| | | | |
|---|---|---|---|
| 2,907,320 | 10/1959 | Weese et al. | 128/725 |
| 3,511,237 | 5/1970 | Jaeger | 128/720 |
| 3,621,833 | 11/1971 | Crane | 128/720 |
| 3,726,271 | 4/1973 | Mondshine et al. | 128/720 |
| 4,122,839 | 10/1978 | Franetzki et al. | 128/720 |

FOREIGN PATENT DOCUMENTS

| | | | |
|---|---|---|---|
| 1119459 | 12/1961 | Fed. Rep. of Germany | 128/720 |
| 197710 | 10/1977 | U.S.S.R. | 128/720 |

OTHER PUBLICATIONS

Pimmel et al., "Inst. for Resp. Impedance . . . ", IEEE Trans. on Biomed. Eng., vol. 24, No. 2, Mar. 1977.

*Primary Examiner*—Lee S. Cohen

[57] ABSTRACT

Apparatus for measuring the respiratory resistance of a patient has a passageway for the flow of air produced by the patient's exhalation and a valve for temporarily halting and then restoring the flow. The rate of flow following the temporary halting depends solely upon the respiratory resistance. Respiratory resistance is derived from circuitry responsive to signals representing pressure and rate of flow. The rate of flow is preferably derived from a comparison of the pressure within the apparatus with the ambient pressure. Provision may be made for actuating the valve automatically when satisfactory conditions are established, for visual display of the resistance and for averaging the resistance results over a number of exhalations.

6 Claims, 2 Drawing Figures

APPARATUS FOR THE DETERMINATION OF RESPIRATORY PARAMETERS

The present invention relates to apparatus for the determination of respiratory parameters.

For some diagnostic purposes, it is useful to measure the respiratory resistance of a patient, a parameter which depends upon the condition of the alveoli and larger airways.

In accordance with the present invention, there is provided apparatus for measuring the respiratory resistance of a patient which comprises a passageway for receiving the flow of air produced by the patient on exhalation, a valve operable, whilst actuated, substantially to halt said flow, actuating means for actuating the valve, a pressure transducer responsive to pressure in the passageway to provide a pressure signal representing the pressure in the passageway, means for generating a flow signal representing the rate of flow of said air, and computer means responsive to the value of the pressure signal and to the flow signal to derive an output representing flow resistance.

Advantageously the actuating means is responsive to the flow signal. This arrangement renders the apparatus automatic in its operation so that there is no requirement for an operator to actuate the valve at a time when the patient is judged to be producing a suitable rate of air-flow.

When the air-flow is stopped, or substantially stopped, the pressure within the respiratory system tends to become uniform throughout. On re-starting the flow the resistance to flow depends solely upon the patient's respiratory resistance but, as the flow continues, this condition is lost as pressure differentials develop within the system. Although it would be expected that the most useful measurement of resistance is one taken immediately on re-starting, it is found that a clinically more meaningful result is given by a delayed measurement obtainable, in accordance with the invention, by having the computer means responsive to the value of the pressure signal at a pre-determined interval after actuation of the valve. In practice, the interval is preferably from 0.25 to 0.52 second, the optimum interval being 0.4 second.

Any desired arrangement may be provided for providing the flow signal required together with the pressure signal for derivation of the flow resistance by the computer. Mechanical devices, eg. a rotor driven by the air-flow, are best avoided because of the speed at which the flow signal is required and because of the difficulty of processing a mechanical output signal. A thermistor exposed to and cooled by the air-flow may be employed to give an electrical output subject to having the requisite robustness of construction and smallness of thermal capacity. It is found that satisfactory results can be obtained by having the means for generating the flow signal responsive to the pressure signal of the transducer (or a second transducer exposed to the interior of the passageway) and to the ambient pressure. A separate ambient pressure transducer may be provided for this purpose, but it is preferred to provide a differential transducer or two transducers mounted together for response to the pressure in the passageway and the ambient pressure. A separate ambient pressure transducer may be provided for this purpose, but it is preferred to provide a differential transducer or two transducers mounted together for response to the pressure in the passageway and the ambient pressure. This arrangement gives a simple and robust construction.

Although in using pressure in the passageway it is necessary to provide resistance to the flow of air from the passageway whilst the valve is not actuated, in order to produce a flow signal, it is found that there is little interference with the validity of the measurements obtained.

In a preferred apparatus, the flow passageway is built into a head, conveniently positionable with respect to the patient, irrespective of posture, and the head also mounts the flow-halting valve, an electrical relay or other actuator for the valve, and the transducer or transducers preferably with a pre-amplifier. The remainder of the equipment is separately mounted and connected with the head by a cable.

The computer means conveniently has a digital output, preferably supplying a digital display. Its circuit is readily arranged to provide command signals for the valve when the patient is providing an appropriate rate of air flow; for this purpose, the flow signal generating means may be operated continuously or substantially continuously between flow-resistance measurements.

The following description of a preferred embodiment of the apparatus in which reference is made to the accompanying drawings is given in order to illustrate the invention.

Figure 2:
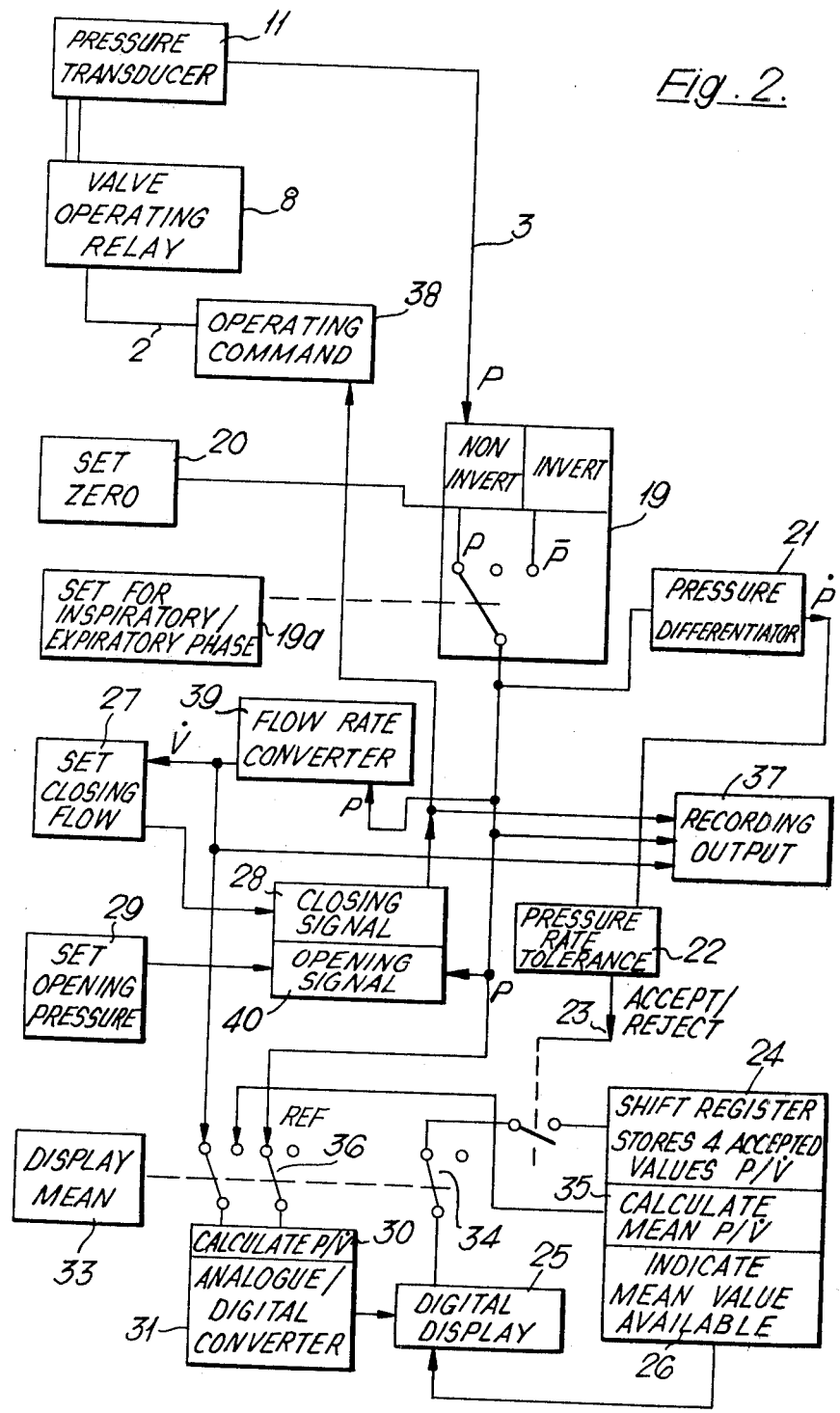

In the drawings:

FIG. 1 shows a part of the apparatus, said part having a flow passageway, a valve operating relay and a pressure transducer, and FIG. 2 shows the relay, the transducer, and the remainder of the apparatus in diagrammatic form.

The part of the apparatus shown in FIG. 1 is a head connected with the remainder of the apparatus via a multi-core connecting lead 1 which provides the signal routes 2 & 3 (FIG. 2) and a power supply from a power source, not shown.

Within the head of FIG. 1 is a flow passageway 4 to the inlet end 5 of which is connected a mouthpiece, shown in part at 26. At the opposite end of passageway 4 is an outlet port 5' which is closable by a flap valve 6 mounted on an actuating arm 7, said arm being part of a valve operating relay 8.

A side port 9 of passageway 4 is connected via a tube 10 to a pressure transducer 11. This transducer has a diaphragm 12 which is exposed on one side to the pressure in tube 10 via a passageway 111 and on the other side to the ambient pressure via a passageway 112 leading from an open port 13. Transducer elements 14 and 15 located one on each side of the diaphragm and compactly mounted with a pre-amplifier system 16, as shown, and perhaps an amplifier 17, provide a differential pressure output.

The output of the pre-amplifier system 16 is a function of the difference between the pressure in passageway 4 and the ambient pressure. With the flap valve 6 in the open position, the resistance to flow of exhaled air outwardly through port 5 is sufficient to maintain the pressure in passageway 4 high enough to enable a usable output signal, representing rate of flow, to be obtained from the pre-amplifier system 16. At the same time however, the resistance is low enough to have no unacceptable effect upon the rate of flow itself.

Energisation of the relay 8 via an amplifier mounted in the control unit closes the flap valve 6 to halt the flow through passageway 4 for the purpose hereinbefore described.

The computing and control system, which is constructed from commercially available components including logic and display circuits is shown diagrammatically in FIG. 2. An amplified signal P from the pressure transducer 11 is either inverted ($\bar{P}$) or non-inverted (P) as selected by the inspiration or expiration switch 19 operable manually by setting the inspiratiory/expiratory phase control 19a. The set zero button 20 is used to zero the output signal from the pressure transducer 11 before commencing a test. The signal P (or $\bar{P}$) is passed to the pressure differentiator 21 which produces the differentiated signal $\dot{P}$. $\dot{P}$ is then checked by comparator 22 to see that it is within tolerance. If the signal is unacceptable the electronic switch 23 to the analog shaft register 24 opens preventing the signal from being stored. In this instance a 0.0 reading will be shown on the digital display 25.

Pressure P is also fed to the flow rate converter 34. This unit converts pressure into flow rate $\dot{V}$, which is monitored by the set closing flow unit 27. When the actual flow $\dot{V}$ equals the set value of closing flow the interruptor valve 6 is closed by a closing signal generated at 28 and supplied to relay 8 through operating command control 38. The pressure in the transducer then builds up until it equals the set opening pressure, determined by the setting of unit 29, at which point the valve 6 is opened by an opening signal generated at 40.

Both P and $\dot{V}$ are fed to calculator 30 to calculate P/$\dot{V}$ and through analogue to digital converter 31 to the digital display 25. The signal is converted back to analogue form for storage in the shaft register 24 which can accept up to four values. When four acceptable values of P/$\dot{V}$ are stored, two horizontal bars signalled by an indicator circuit 26 are illuminated on the display 25. By pressing the display mean button 33, which actuates change-over switches 34 & 36, the mean value of these four acceptable readings calculated by circuit 35 can be digitised by converter 31 and shown on display 25.

Outputs provided at 37 may be employed to provide a permanent recording of the generated data if required. Operating command control 38 enables the operator to start or stop response of the valve 6 to the opening and closing signals as required.

It will be understood that the construction of the computing display and control system may be varied by those skilled in the art once the requirements thereof have been appreciated. The construction may be varied, for example, to comply with the prevailing conditions of the availability and cost of components.

We claim:

1. Apparatus for measuring the respiratory resistance of a patient, said apparatus comprising:
   (a) a body part formed with a passageway for receiving a flow of air produced by an exhalation by the patient,
   (b) a normally open, closable valve operable and arranged, when open, to permit passage of said flow through said passageway and, when closed, substantially to halt said flow,
   (c) actuating means responsive to receive opening and closing signals to open and close said valve,
   (d) means, including a pressure transducer responsive to the pressure of flow in said passageway, for providing said actuating means with a closing signal to close said valve when said pressure reaches a predetermined level during exhalation, and an opening signal subsequent to said closing signal to reopen said valve during said exhalation, and
   (e) means responsive to the output of said transducer generating a flow signal representing the rate of flow of said flow of air when said valve is reopened.

2. Apparatus according to claim 1, in which said valve is arranged to provide, when open, a residual resistance to the flow which is sufficient to maintain pressure within said passageway adequate for the transducer to respond thereto.

3. Apparatus according to claim 2, wherein the pressure transducer is a differential pressure transducer responsive to both pressure in said passageway and to ambient pressure, to produce said flow signal.

4. Apparatus according to claim 1, in combination with processing means responsive to the flow signal generating means to provide an output representing the respiratory flow resistance of the patient after said valve is reopened.

5. Apparatus according to claim 4, in which said processing means includes means for storing a plurality of respiratory resistance outputs and display means for displaying the average of said plurality.

6. Apparatus according to claim 1, in combination with processing means responsive to said flow signal generating means to provide an output representing the respiratory resistance of the patient after said valve is reopened, visual display means for said output, and means providing opening and closing signals for said actuating means independently of said transducer, and in which the means generating said flow signal includes a preamplifier.

* * * * *